United States Patent [19]

Howard et al.

[11] 4,359,596

[45] Nov. 16, 1982

[54] LIQUID SALT EXTRACTION OF AROMATICS FROM PROCESS FEED STREAMS

[75] Inventors: Kent A. Howard; Howard L. Mitchell; Robert H. Waghorne, all of Baton Rouge, La.

[73] Assignee: Exxon Research and Engineering Co., Florham Park, N.J.

[21] Appl. No.: 289,324

[22] Filed: Aug. 3, 1981

[51] Int. Cl.$^3$ .............................................. C07C 7/17
[52] U.S. Cl. .................................... 585/856; 585/833; 585/860; 585/863; 585/864
[58] Field of Search ............... 585/833, 860, 863, 864, 585/856

[56] References Cited

U.S. PATENT DOCUMENTS

| | | | |
|---|---|---|---|
| 289,323 | 8/1981 | Mitchell . | |
| 3,206,377 | 9/1965 | Cornell et al. | 585/864 |
| 3,345,287 | 10/1967 | Voetter et al. | 585/864 |
| 3,929,849 | 12/1975 | Oswald | 260/448 C |
| 3,954,821 | 5/1976 | Herskovitz et al. | 260/429 R |
| 4,008,281 | 2/1977 | Knowles et al. | 568/13 |
| 4,013,700 | 3/1977 | Cawse | 518/701 |
| 4,053,493 | 10/1977 | Oswald | 260/448 C |
| 4,136,103 | 1/1979 | Oswald | 260/448 C |

FOREIGN PATENT DOCUMENTS 7820035  8/1978  European Pat. Off. .

OTHER PUBLICATIONS

PCT International Publication WO 80/01692 (published Aug. 21, 1980).
PCT International Publication WO 80/01690 (published Aug. 21, 1980).
PCT International Publication WO 80/01689 (published Aug. 21, 1980).
Tetrahedron Letters, vol. 21, pp. 3037–3038.

*Primary Examiner*—Thomas A. Waltz
*Assistant Examiner*—A. Pal
*Attorney, Agent, or Firm*—Robert J. North

[57] ABSTRACT

Liquid salts such as quaternary phosphonium and ammonium salts of halides, acids, or more complex anions can be utilized to extract aromatics from mixed aliphatic/aromatic hydrocarbon feeds such as isomerization process feed streams, cat naphthas, lube stocks, and the like. Such salts show the required solubilities in various solvents to exhibit a distinct selectivity advantage over more commonly used extraction solvents such as sulfolane in the extraction of benzene and other aromatics from heptane and other aliphatic feedstreams.

14 Claims, No Drawings

LIQUID SALT EXTRACTION OF AROMATICS FROM PROCESS FEED STREAMS

BACKGROUND OF THE INVENTION

This invention relates to a process for the extraction of aromatics from mixed aliphatic/aromatic hydrocarbon feeds such as isomerization process feed streams, cat naphthas, lube stocks, and the like. More particularly, this invention is concerned with the use of liquid salts, in particular, quaternary ammonium, phosphonium and arsonium salts of halides, acids, or more complex anions, as extracting agents for aromatics from paraffin feedstreams. Such salts show the required solubilities in various solvents and low volatility to allow for a distinct selectivity advantage over more conventional solvents, particularly sulfolane, which is commercially used. Such salts also show the exceptionally low volatilities typical of salts, thus minimizing losses by vaporization and facilitating recovery of extractate.

In certain instances, aromatics in hydrocarbon feedstreams can act as catalyst poisons such as in isomerization feedstreams. Then, the aromatics must be removed prior to the paraffin isomerization reaction. In this instance, sulfolane cannot be used since it is partially miscible with the paraffinic hydrocarbon and would also tend to poison the isomerization catalyst. By contrast, liquid salts which have a high affinity for aromatic hydrocarbons and are insoluble in the paraffinic hydrocarbon/carrier, are excellent extractants since they are readily separated from the paraffinic hydrocarbon feedstream and pose no catalyst poisoning hazard.

Specific objects of this invention are to provide a process utilizing liquid salts, having a high extractive selectivity for aromatic compounds and high solvation capacity, are readily synthesized from low cost, readily available materials, and can easily be stripped or separated from the extraction phase, and which have high thermal and chemical stability.

SUMMARY OF THE INVENTION

In accordance with the present invention, there is provided a process for extracting aromatic hydrocarbons from a mixed aliphatic/aromatic feed comprising the step of contacting said feed with a solvent comprising a liquid salt of the formula:

[R$_4$Q][A]

wherein Q is N, P or As; A is a monovalent or polyvalent anion; R$_4$Q is a monovalent or polyvalent cation in sufficient number to render the salt electrically neutral; R is a hydrocarbon radical independently selected from the group consisting of linear or branched $C_1$–$C_{20}$ alkyl, $C_5$–$C_{10}$ cycloalkyl, $C_7$–$C_{20}$ aralkyl and alkaryl, and $C_6$–$C_{10}$ aryl, including inert or unreactive substituents thereon, and mixtures thereof, wherein the total number of carbon atoms in the four R radicals is at least 16, and wherein not more than one R radical being methyl, and wherein said contacting step is performed above the melting point and below the decomposition point of said liquid salt.

Preferred embodiments of the process include the anion of the liquid salt being chosen to further enhance the selectivity and capacity of the liquid salt phase for aromatic hydrocarbons while excluding paraffin hydrocarbons.

DETAILED DESCRIPTION OF THE INVENTION AND PREFERRED EMBODIMENTS

The process of the present invention is directed to the extraction of aromatic hydrocarbons such as benzene, toluene and xylene from mixed aliphatic/aromatic hydrocarbon feeds by the use of liquid salts.

A particular benefit of the use of the liquid salt solvent system for extraction of aromatics is the adaptability of the solvent system to the needs and requirements of petroleum or petrochemical processing and the changing economics associated with the world energy needs. The variety of such liquid salt solvents is very great, especially with the additional variabilities associated with mixtures, combinations with cosolvent acids and water. Thus, there are considerably greater degrees of freedom for optimization in the liquid salt solvent system for aromatics extraction than are available in the relatively "simple" extraction systems such as the sulfolane solvent system. There are very cheap and very expensive salts, and among the cheaper salts are a wide variety of materials with widely varying properties. Thus, an economical salt solvent system can be tailored for each particular processing need, e.g., removal of the last traces of aromatics from a paraffin isomerization feedstreams, or removal of large quantities of aromatics from rich feedstreams for recovery of the aromatics for use as solvents or chemical feedstocks.

By the term "liquid salt" is meant a molten fluid at the temperature of extraction, from about room temperature to about 400° C., in which the solvent is present above its melting point and below its decomposition point, and can be a clear, pourable fluid or melt. In any event, contacting rthe liquid salt with the mixed aliphatic/aromatic hydrocarbon feed produces a two-phase system, with the extracting phase usually being the more dense and lower phase or in which the extractant phase may be present as droplets or particles or "bubbles" of separate phase suspended within the liquid from which the aromatics are being extracted.

The novelty of the process lies in the use of liquid salts as solvents and their characteristics properties, and specifically their use to extract aromatic hydrocarbons from liquid hydrocarbon streams into the immiscible solvent. In general, the liquid salts should have high extractive selectivity and high extractive capacity for aromatic hydrocarbons, should be readily synthesizable from low cost, readily available materials, should be easily stripped or separated from the extraction phase, and should possess high thermal and chemical stability. Further, they should be substantially immiscible with liquid paraffin hydrocarbons and be characterized by relatively low viscosity. As salts, they possess exceptionally low volatility allowing excellent extractate recovery by stripping with steam or other gas stream or by distillation, without loss of solvent and without contamination of the recovered extractate with solvent.

These properties are met by liquid salts of the above-described general formula in which the salt is electrically neutral with the appropriate number of anions to balance the number of cations, and the R hydrocarbon radicals are independently selected from the groups described above.

It has been found that operable and efficient liquid salts in the process should possess at least 16 total carbon atoms in the combination of all four R hydrocarbon radicals per cation, only one of which can be methyl and preferably in which all four R radicals per cation are not identical. The maximum number of carbon atoms per R group is about 20. Preferably, the number of carbon atoms is 17 or more per cation, and branched alkyl chains are preferable to straight alkyl chains. Also preferably, the maximum number of carbon atoms per total cation is about 30 and particularly long or large single substituents are less preferred due to greater viscosity and poor solubility characteristics because the solvent salt becomes more surface active and has a greater tendency to form emulsions with consequent difficulties in separation of the two phases. Mixtures of salts either of cation or anions or both are preferred over the use of pure or neat materials and the presence of some aromatic, multiply-bonded moieties or chloride substituents are preferred for their interactions with the aromatic extractate molecules, if within the stability range of use. Preferably, the maximum number of cations in single liquid salt moiety is two. Quaternary cations are necessary in the process while tertiary, secondary or primary cations are inoperable due to gradual decomposition of the salt. Quaternary phosphonium cations are most preferred in the process over the entire applicable temperature range while quaternary ammonium salts are less preferred than those of P or As due to poorer stability in general.

Representative R radicals include methyl, ethyl, propyl, n-butyl, sec-butyl, t-butyl, n-pentyl, 2-methylbutyl, 3-methylbutyl, n-hexyl, n-octyl, 2-ethylhexyl, decyl, stearyl, dodecyl, cyclohexyl, p-chlorobenzyl, benzyl, p-methylbenzyl, 2-phenethyl, tolyl, p-xylyl, phenyl, chlorophenyl, trifluorobutyl, n-eicosanyl, cyclohexylbutyl, p-dodecylphenyl, phenylbutyl, butylphenyl, naphthyl, and the like. The R radicals may also be substituted with substituents inert under the process conditions such as $C_1$-$C_4$ alkoxy, $C_6$-$C_{10}$ aryloxy and the less reactive halogens, F and Cl.

Particularly preferred R radicals are n-butyl, p-tolyl, 2-ethylhexyl, phenyl, p-chlorophenyl, 3-methylbutyl, benzyl, and n-octyl moieties.

Representative cations formed from different combinations of said R radicals include, tetra-n-butylphosphonium, tetra-iso-butyl-phosphonium, tri-n-butyl-3-methylbutylphosphonium, tri-n-butyl-2-methylbutylphosphonium, tri-n-butyl-2-ethylhexylphosphonium, tri-n-butyl-n-octylphosphonium, tri-n-butylcyclohexylphosphonium, tri-n-butylphenylphosphonium, tri-n-butylbenzylphosphonium, tri-n-butyl-p-methylbenzylphosphonium, methyl-tri-n-octylphosphonium, tri-n-butyl-3-methylbutylarsonium, tri-n-butyl-3-methylbutylammonium, tetra-n-butylammonium, tri-n-butylphenylammonium, tri-n-butyl-p-tolylphosphonium, tri-n-butyl-s-butylphosphonium, n-butyltri-n-octylphosphonium, n-butyltri-n-octylammonium, tri-n-butylstearylphosphonium, alpha,alpha-bis(tri-n-butylphosphonium)para-dimethylbenzene, and the like. The above representative cations are preferred in low temperature extractions, i.e., from 25°–225° C.

Cations which were found to be inoperable in the process or gave highly unsatisfactory results are dimethyldi-n-octylphosphonium, dimethyldi-n-hexylphosphonium, dimethyldi-n-decylammonium, and tri-n-butylpropylphosphonium, di-n-butyldistearylphosphonium, octabutyltriethylenetriammonium, trioctylammonium, trioctylphosphonium and tricyclohexylphosphonium.

Representative anions useful in the process include halide; bromide, chloride, fluoride; sulfate, sulfonate, carbonate, naphthenate, bicarbonate, bisulfate, $C_1$-$C_{20}$ alkylsulfonate, including methanesulfonate, trifluoromethanesulfonate, dodecylsulfonate, phosphonate, benzenephosphonate, tetra-n-butylboranate, $C_1$-$C_{20}$ alkylcarboxylate, including acetate and 2-ethylhexanoate, benzenesulfonate, p-toluenesulfonate, p-chlorobenzenesulfonate, phenoxybenzenesulfonate, benzenephosphinate, benzoate, tetrachloroaluminate, tetrafluoroborate, hydroxide, methoxide, phenoxide, 2,4,6-tri-t-butylphenoxide, tris(2-methoxyethoxy)acetate, tetra-2-ethylhexylboranate, tetra-sec-butylboranate, triethyl-2-ethylhexylboronate, and the like. The aforementioned anions are preferred for use in low temperature extraction processes. Particularly preferred organic anions include methanesulfonate, trifluoromethanesulfonate, benzenesulfonate, benzenephosphonate, and p-chlorobenzenesulfonate. Less preferred are the inorganic anions, due to their lower capacities for aromatics and higher affinities for water, however, their lower costs make them preferred in some situations.

Representative examples of preferred liquid salts include: tri-n-butylbenzylphosphonium chloride, bromide, methanesulfonate, benzenesulfonate, p-tolylsulfonate, and tetrafluoroborate; tri-n-butyl-2-ethylhexylphosphonium chloride, bromide, 2-ethylhexanoate, naphthenate, methanesulfonate, benzenesulfonate, p-tolylsulfonate and tetrachloroaluminate; tri-n-butyl-3-methylbutylphosphonium tetra-n-butylboranate, 2-ethylhexanoate, naphthenate, acetate, bromide, methanesulfonate, and benzenesulfonate; tri-n-butyloctylphosphonium chloride, bromide, methanesulfonate, benzenesulfonate, p-tolylsulfonate, and tetra-n-butylboranate; tetra-n-butylammonium tetrabutylboranate, 2-ethylhexanoate, naphthenate, bromide, and chloride; tri-n-butylphenylphosphonium methanesulfonate, benzenesulfonate, benzenephosphinate, bromide, di-n-butylphenyl-3-methylbutylphosphonium methanesulfonate and chloride; tri-3-methylbutyl-2-ethylhexylphosphonium tetrachloroaluminate and trichloroiodoaluminate; tetra-n-butylphosphonium chloride, bromide, methanesulfonate, trifluoromethanesulfonate, trichloromethanesulfonate, benzenesulfonate, p-toluenesulfonate, p-chlorobenzenesulfonate, phenylphosphonate, tetra-n-butylboranate, acetate, benzoate, 2-ethylhexanoate, sulfate, phosphate, tetrachloroaluminate and pentafluorophenoxide; and phenyltricyclohexylarsonium iodide. Particularly preferred are the entire group of phosphonium salts due to their exceptional stability and their ease of manufacture.

Melting points of the operable salts or salts which are functional as components of operable mixtures range from about −80° to 225° C. and some only form glossy solids with no readily definable melting point. Particularly prevalent among the group forming only glossy solids or mixed glossy and crystalline solids are the mixed salts. Such mixed salts, containing mixed cations, mixed anions, or both are preferred due to generally lower viscosities and lower melting points or no melting points. In like manner, cations with mixed R groups are preferred, as are those with branched chain R groups and other substituents which help to promote molecular and ionic disorder. The most preferred salt or mixture melting points are below 35° C. if there is any "melting point" at all. Decomposition points range from about 150° to 400° C., with most being between 225° and 325° C., due to the aliphatic carbons attached to the heteroatoms of the cations. The general order of stability of cations, according to the heteroatom Q is P>>As>N with individual cations differing with the R groups, and with some overlap between groups, due to the greater or lesser amounts of stabilization, due to R groups, nucleophillicity of anions, etc. For thermal stability, an aromatic R attached directly to the heteroatom is particularly preferred. Likewise, the presence of some water is preferred to promote stability, presumably because it decreases the nucleophillicity of the anions, particularly the halides.

The extracting "solvent" in the subject process comprises a liquid salt, as described hereinabove, and can also comprise a small amount of cosolvent or cosolvents for the liquid salt, such as water, or the corresponding acid of the anion radical. Water is useful as a cosolvent since it is inexpensive, relatively non-corrosive and can increase selectivity in the extraction. Acids of anions are preferred as cosolvents since they can increase not only selectivity toward aromatics, but also extraction capacity. Mixtures of cosolvents are likewise useful and preferred. A mixture of water and the acid or acids of the anions of the liquid salts is particularly preferred.

Representative examples of corresponding acid cosolvents include sulfuric acid, methanesulfonic acid, benzenesulfonic acid, p-toluenesulfonic acid, p-chlorobenzenesulfonic acid, phosphoric acid, benzenephosphinic acid, benzenephosphonic acid, phenoxybenzenephosphonic acid, benzenephosphorous acid, tetrachloroaluminic acid, tetrafluoroboric acid, methanol, phenol, and the like. If a cosolvent is used, it is present in no more than 25 volume percent of the liquid salt solution formed by the cosolvent and liquid salt, preferably no more than 15 volume percent, and most preferably less than about 5 volume percent. The minimum amount of cosolvent or cosolvents needed for stability, selectivity, or capacity is most preferable because additional product separation problems and corrosion problems are incurred by the use of at least some cosolvents.

The process of the extraction can be conducted in the temperature range of about 25° to 400° C., preferably below 325° C., and most preferred below 225° C. The use of elevated pressures is sometimes necessary to maintain the feedstream hydrocarbons in the liquid state, however, at ordinary pressures, e.g., ambient to about 1000 atmospheres, the extraction process is essentially independent of pressure.

In those cases where the process is conducted from 25° to 225° C., preferred salts are where Q is nitrogen or phosphorous, the total number of carbon atoms in said four R groups is 17, three of said R groups are identical and said R groups are selected from $C_6$-$C_{20}$ aryl-containing and $C_1$-$C_{20}$ linear or branched alkyl. Thus, in low temperature extraction, preferably, the process requires tetraalkyl- or aryltrialkylammonium and phosphonium salts.

Particularly preferred salts in the low temperature extraction process are tri-n-butyl-n-octylphosphonium, tri-n-butylphenylphosphonium, tri-n-butyl-2-ethylhexylphosphonium, tri-n-butylbenzylphosphonium, and tri-n-butyl-3-methylbutylphosphonium cations or mixtures with methanesulfonate, benzenesulfonate, chloride, bromide, trifluoromethanesulfonate, benzenephosphonate, sulfate, and phosphate anions or mixtures.

The liquid salts operable in the subject process can be easily synthesized from low cost, readily available materials using known procedures. One synthetic procedure that can be employed involves addition of phosphine to alpha-olefins according to the following general equations:

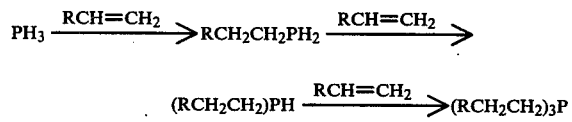

The quaternization of the trialkyl phosphines of the prior equations can be accomplished by known methods, including reacting the trialkylphosphine with a reactive material, for example, an alkyl halide or a sulfonic acid ester to yield the corresponding salt. Mixtures can readily be made by utilizing mixed olefins, mixed halides, mixed cosolvent acids, etc.

The extractive utility of the liquid salts of the subject process is a function of the ability of the liquid salts or their mixtures with cosolvents to be miscible with desired aromatic hydrocarbons to be extracted while remaining immiscible with aliphatic hydrocarbon compounds; thereby allowing for the solvation of the aromatics in the salts and the removal of the aromatics from the aliphatic hydrocarbon streams. This miscibility of aromatic hydrocarbons and immiscibility of the aliphatic hydrocarbons with the salts of the present invention is partially governed by the length of the substituent groups attached to the quaternary cationic and anionic nuclei. In general, the effect of increasing the alkyl chain length above the middle range of the operable R groups of the cation is seen to increase miscibility with aliphatic hydrocarbons thus decreasing the selectivity toward the more polar aromatic molecules.

Liquid salt cations with total carbon numbers in the range 17 through 22 are highly preferred and even more greatly preferred in combination with anions which contain at least some organic portion, in the range of $C_1$ to $C_{16}$.

The liquid salts of the subject process show thermal and chemical stability over a wide range of operating conditions. In general, phosphonium salts are much more stable than corresponding ammonium salts. The halides are generally low-melting solids at room temperature compared to sulfonates, which are liquids at room temperature.

The process of the instant invention is conducted by contacting a mixed aliphatic/aromatic hydrocarbon feed with a liquid salt, described herein, at a temperature above the melting point and below the decomposition temperature of the salt and preferably at a temperature from 25° to 400° C., and more preferably at the temperature where aromatic extraction is maximized for the particular salt being used, the quantity and type of aromatics in the feed, etc.

Generally, for most aromatics, the extraction temperature will be from about 25° to 200° C. to aid in combatting the volatility of the aromatic compounds at high temperatures.

The amount of liquid salt "solvent" used in the extraction process is not fixed and convenient amounts which can be employed are in the range of 0.5 to 5 volumes of liquid salt solvent per volume of hydrocarbon feed as the liquid. Generally, and preferably, about 1 to 2 volumes of extracting agent per volume of liquid hydrocarbon feed are used. The relative volumes of solvent to feed are chosen, depending on the amount of aromatics in the feed, the desired level of aromatics in the raffinate, the characteristics of the particular salt solvent in use, and the effectiveness of the extract separation process chosen.

In general, the extracting solvent will be able to contain from about 5 volume percent up to about 25 volume percent of aromatic hydrocarbon per volume of liquid salt, with negligible up to as much as 10 volume percent aliphatic hydrocarbons.

The extraction process can be batch or continuous, including countercurrent extraction, and the like. The extraction process can also be via liquid membrane processes.

Apparatus for conducting the process are conventional and can be a separator funnel on a laboratory scale to large industrial size extraction equipment.

The ease of separation of the liquid salt from the aliphatic hydrocarbon is also an important characteristic the salt should possess. This characteristic becomes extremely important when it is desired to reduce the concentration of the aromatic in the hydrocarbon feed to extremely low concentrations. By contrast, it is difficult to achieve an essentially aromatic-free solvent concentration with conventional liquid solvents, such as sulfolane, because of their volatility.

In contrast, the organic salts of the present process do not encounter the same problem as conventional solvents because of the salt's low volatility. This makes recovery of all of the extracted aromatic from the salt possible by distillation, steam stripping, gas stripping, and the like.

There are several measures of extraction efficiency which are important in the determination of the utility of a given liquid salt extractant. One of these measures is selectivity, which is a measure of the extent of separation of the two components being separated. Selectivity, $\beta$, is defined by the following equation:

$$B = \frac{\left(\frac{\text{benzene}}{\text{heptane}}\right) \text{extract}}{\left(\frac{\text{benzene}}{\text{heptane}}\right) \text{raffinate}}$$

wherein the extract is the salt rich phase, and the raffinate is the product or feed residue or aliphatic rich phase. Benzene and heptane are used here as examples of aromatic and aliphatic materials.

Another measure of solvent extraction efficiency is capacity, which is defined as the weight fraction of the aromatic hydrocarbon in the liquid salt at equilibrium. This parameter provides an indication of how much solvent is necessary to extract a given amount of hydrocarbon from an aliphatic stream.

The following example is illustrative of the best mode of carrying out the instant invention, as contemplated by us, and should not be construed as being a limitation on the scope or spirit of the instant invention.

EXAMPLE

In order to test the extractive efficiency of the process of the present invention, four liquid phosphonium salts, among others, were synthesized and compared to sulfolane in extraction experiments. The salts employed were tri-n-butyl-2-ethylhexylphosphonium chloride, tri-n-butyl-n-octylphosphonium bromide, tri-n-butyl-phenylphosphonium methanesulfonate with 4.5 volume percent methanesulfuric acid, 0.3 volume percent $H_2O$ and tri-n-butyl-3-methylbutylphosphonium benzenesulfonate with 4.1 volume percent benzenesulfonic acid, 0.8 volume percent $H_2O$.

The apparatus for the extractions was developed with two objectives in mind: keeping the time to reach equilibrium at a minimum, and facilitating sampling of both phases in the extraction vessel. The apparatus consisted of a 200 milliliter flask fitted with reflux condenser and a temperature-controlled oil bath, magnetic stirrer, an inlet for an inert atmosphere. The flask was charged with equal volumes (50 cc) of solvent and a feed solution made up as 10 volume percent benzene and heptane. The separate phases were stirred vigorously for a specified time, allowed to separate and the supernatant raffinate decanted. Comparative benzene concentrations were determined for feed and raffinate by infrared spectroscopy. The ratio of benzene to heptane in solvent was determined by gas chromatography retention. From these data, a measure of extractive capability was determined. Table summarizes the results of the above-mentioned experiments. As can be seen, the selectivity values for tri-n-butyl-2-ethylhexylphosphonium chloride, tri-n-butyl-n-octylphosphonium bromide were all significantly higher than those for sulfolane. The capacities of the two sulfonate salt mixtures were also higher than those for sulfolane.

For some purposes, the costs of the solvent material, in particular, the tetraalkylphosphonium salts are particularly preferred as solvents for extraction of aromatics, whereas for other purposes the aryltrialkylphosphonium salts are particularly preferred as solvents for aromatics extraction. The same is likewise true for the analogous quaternary ammonium salts which are less preferred than the phosphonium salts due to their stabilities, etc.

TABLE

BENZENE/HEPTANE IN SOLVENT DETERMINED BY GC RETENTION
USING A UC W-98 COLUMN, 15 cc/min, FID[a], 68° C.

| Solvent | T °C. | Contact Time, hr. | B/H[b] EXTR | B/H[c] RAFF | % HC[d] EXTR | B[e] |
|---|---|---|---|---|---|---|
| Sulfolane | 25 | 2 hr. | 0.26 | 0.070 | 1.02 | 3.7 |
|  |  | 6 hr. | 0.55 | 0.052 | 3.84 | 10.6 |
| $P_{4442ethex}Cl$[f] | 25 | 2 hr. | 2.39 | 0.076 | 2.26 | 31.4 |
| $P_{4448}Br$[g] | 54 | 2 hr. | 3.38 | 0.068 | 1.98 | 49.7 |
| $P_{444}PhCH_3SO_3$[h] | 52 | 2 hr | 11.21 | 0.039 | 4.99 | 287. |

TABLE-continued
BENZENE/HEPTANE IN SOLVENT DETERMINED BY GC RETENTION USING A UC W-98 COLUMN, 15 cc/min, FID[a], 68° C.

| Solvent | T °C. | Contact Time, hr. | B/H[b] EXTR | B/H[c] RAFF | % HC[d] EXTR | B[e] |
|---|---|---|---|---|---|---|
| $P_{444mb}PhSO_3$[i] | 49 | 2 hr. | 9.47 | 0.042 | 5.62 | 225. |

[a]FID = Flame Ionization Detector
[b]benzene/heptane weight fraction in extract.
[c]benzene/heptane weight fraction in raffinate.
[d]% hydrocarbons in the extract.
[e]as defined above.
[f]tri-n-butyl-2-ethylhexylphosphonium chloride.
[g]tri-n-butyl-n-octylphosphonium bromide.
[h]tri-n-butylphenylphosphonium methane sulfonate with 4.5 vol. % methanesulfonic acid and 0.3 vol. % $H_2O$.
[i]tri-n-butyl-3-methylbutylphosphonium benzenesulfonate with 4.1 vol. % benzenesulfonic acid and 0.8 vol. % $H_2O$.

What is claimed is:

1. A process for extracting aromatic hydrocarbons from a mixed aliphatic/aromatic feed comprising the step of contacting said feed with a solvent comprising a liquid salt of the formula:

[R4Q][A]

wherein Q is N, P or As; A is a monovalent or polyvalent anion; $R_4Q$ is a monovalent or polyvalent cation in sufficient number to render the salt electrically neutral; R is a hydrocarbon radical independently selected from the group consisting of linear or branched $C_1$–$C_{20}$ alkyl, $C_5$–$C_{10}$ cycloalkyl, $C_7$–$C_{20}$ aralkyl and alkaryl and $C_6$–$C_{10}$ aryl, including inert or unreactive substituents thereon, and mixtures thereof, wherein the total number of carbon atoms in the four R radicals is at least 16, and wherein not more than one R radical being methyl, and wherein said contacting step is performed above the melting point and below the decomposition point of said liquid salt.

2. The process of claim 1 wherein three of said R radicals are identical.

3. The process of claim 1 wherein said R radicals are selected from methyl, ethyl, propyl, n-butyl, n-pentyl, isopentyl, hexyl, n-octyl, 2-ethylhexyl, decyl, dodecyl, stearyl, benzyl, p-methylbenzyl, p-chlorobenzyl, cyclohexyl, 2-phenethyl, p-tolyl, phenyl, p-chlorophenyl, p-xylyl 3-methylbutyl, and mixtures thereof.

4. The process of claim 1 wherein the total number of carbon atoms in the four R radicals is 17-30.

5. The process of claim 1 wherein said cation is selected from tetra-n-butylphosphonium, tetra-isobutylphosphonium, tri-n-butyl-3-methylbutylphosphonium, tri-n-butyl-2-methylbutylphosphonium, tri-n-butyl-2-ethylhexylphosphonium, tri-n-butyl-n-octylphosphonium, tri-n-butylcyclohexylphosphonium, tri-n-butylphenylphosphonium, tri-n-butylbenzylphosphonium, tri-n-butyl-p-methylbenzylphosphonium, methyltri-n-octylphosphonium, tri-n-butyl-3-methylbutylarsonium, tri-n-butyl-3-methylbutylammonium, tetra-n-butylammonium, tri-n-butylphenylammonium, tri-n-butyl-p-tolylphosphonium, tri-n-butylstearylphosphonium, alpha,alpha-bis(tri-n-butylphosphonium)-p-dimethylbenzene, tri-n-butyl-s-butylphosphonium, tri-3-methylbutyl-2-ethylhexylphosphonium, n-butyltri-n-octylammonium, n-butyltri-n-octylphosphonium, and mixtures thereof.

6. The process of claim 1 wherein said anions are selected from halide, sulfate, alkyl or aryl sulfonate, methanesulfonate, benzenesulfonate, naphthenate, carbonate, bicarbonate, bisulfate, $C_1$–$C_{20}$ alkylsulfonate, phosphate, benzenephosphonate, tetrabutyl boranate, $C_1$–$C_{20}$ carboxylate, tetrachloroaluminate, tetrafluoroborate, benzenephosphinate, benzoate, trifluoromethanesulfonate, and mixtures thereof.

7. The process of claim 1 wherein said solvent comprising at least about 85 volume percent liquid salt.

8. The process of claim 1 wherein said process is conducted in the temperature range of from 25° to 400° C.

9. The process of claim 1 wherein said process is conducted in the temperature range of from 25°–325° C.

10. The process of claim 1 wherein said process is conducted in the temperature range of from 25°–225° C.

11. The process of claim 10 wherein Q is N or P, the number of carbon atoms in said four R radicals is at least 17, three of said R radicals are identical and all said four R radicals are selected from $C_1$–$C_{20}$ linear and branched alkyl.

12. The process of claim 11 wherein the cations of said liquid salt are selected from tri-n-butyl-n-octylphosphonium, tri-n-butylphenylphosphonium, tri-n-butyl-2-ethylhexylphosphonium, tri-n-butylbenzylphosphonium, tri-n-butyl-3-methylbutylphosphonium, or mixtures thereof and the anions of said liquid salt are selected from methanesulfonate, benzenesulfonate, chloride, bromide, trifluoromethanesulfonate, acetate, sulfate, benzenephosphonate, phosphate, or mixtures thereof.

13. The process of claim 1 wherein said cation is the tetraalkylphosphonium or monoaryltrialkylphosphonium ion.

14. The process of claim 1 wherein said liquid salt is a mixture of salts defined by said formula.

* * * * *